United States Patent
Plourde et al.

(10) Patent No.: US 10,168,412 B2
(45) Date of Patent: Jan. 1, 2019

(54) DUAL AXIS TRACKING DEVICE

(71) Applicant: WTS LLC, St. Paul, MN (US)

(72) Inventors: Brian Plourde, St. Paul, MN (US); John Abraham, Minneapolis, MN (US); Douglas Plourde, Somerset, WI (US); Richard Pakonen, Birchwood, MN (US); Andy Gikling, St. Paul, MN (US)

(73) Assignee: WTS LLC, St. Paul, MN (US)

(*) Notice: Subject to any disclaimer, the term of this patent is extended or adjusted under 35 U.S.C. 154(b) by 433 days.

(21) Appl. No.: 14/954,091

(22) Filed: Nov. 30, 2015

(65) Prior Publication Data
US 2016/0154082 A1 Jun. 2, 2016

Related U.S. Application Data

(60) Provisional application No. 62/259,748, filed on Nov. 25, 2015, provisional application No. 62/085,699, filed on Dec. 1, 2014.

(51) Int. Cl.
*G01S 3/786* (2006.01)
*G01S 19/01* (2010.01)
(Continued)

(52) U.S. Cl.
CPC .......... *G01S 3/7861* (2013.01); *F16K 24/042* (2013.01); *F24S 20/20* (2018.05);
(Continued)

(58) Field of Classification Search
CPC ..................... F24J 2/07; F24J 2/40
(Continued)

(56) References Cited

U.S. PATENT DOCUMENTS 3,915,148 A 10/1975 Fletcher et al.
4,070,870 A 1/1978 Bahel et al.
(Continued)

FOREIGN PATENT DOCUMENTS

DE 102008040028 7/2010
DE 102012021106 8/2013
(Continued)

OTHER PUBLICATIONS

International Search Report and Written Opinion for related PCT Application No. PCT/US2015/063196 dated May 6, 2016 (19 pages).
(Continued)

*Primary Examiner* — Gregory Huson
*Assistant Examiner* — Nikhil Mashruwala
(74) *Attorney, Agent, or Firm* — Winthrop & Weinstine, P.A.

(57) ABSTRACT

The disclosure relates to a tracking device configured to track an object in space, such as the sun, as the object moves across the sky. The tracking device may further be configured to direct a payload toward the object or toward an angle relative to the object. The tracking device may continuously or intermittently determine the location of the moving object, and adjust the position of the payload accordingly. The tracking device may calculate the position of the moving object based on GPS information, such as triangulated coordinates of the tracking device, date, and time. Generally, the tracking device may be capable of tracking an object such as the sun from anywhere on the earth's surface. The tracking device may employ one or more actuation assemblies to position the payload toward or relative to the moving object. The one or more actuation assemblies may operate through linear motion.

20 Claims, 15 Drawing Sheets

(51) Int. Cl.
*F24S 50/20* (2018.01)
*F24S 30/45* (2018.01)
*F16K 24/04* (2006.01)
*G05D 23/185* (2006.01)
*G05D 3/10* (2006.01)
*F24S 23/74* (2018.01)
*F24S 50/40* (2018.01)
*F24S 20/20* (2018.01)

(52) U.S. Cl.
CPC ............... *F24S 23/74* (2018.05); *F24S 30/45* (2018.05); *F24S 50/20* (2018.05); *F24S 50/40* (2018.05); *G01S 19/01* (2013.01); *G05D 3/105* (2013.01); *G05D 23/1852* (2013.01); *Y02E 10/41* (2013.01); *Y02E 10/45* (2013.01); *Y02E 10/47* (2013.01); *Y02W 10/37* (2015.05)

(58) Field of Classification Search
USPC .......... 126/573, 574, 578; 136/246; 339/853
See application file for complete search history.

(56) References Cited

U.S. PATENT DOCUMENTS

| | | | |
|---|---|---|---|
| 4,269,263 A | 5/1981 | Yukimachi et al. | |
| 5,505,917 A | 4/1996 | Collier, Jr. | |
| 6,959,993 B2* | 11/2005 | Gross | F24J 2/07 126/684 |
| 8,895,836 B2 | 11/2014 | Amin et al. | |
| 9,027,545 B2* | 5/2015 | DeVillier | H02S 20/00 126/600 |
| 9,476,611 B1 | 10/2016 | Shbeeb et al. | |
| 2002/0179138 A1 | 12/2002 | Lawheed | |
| 2006/0201498 A1 | 9/2006 | Olsson et al. | |
| 2007/0215199 A1 | 9/2007 | Dold et al. | |
| 2007/0221362 A1 | 9/2007 | Stewart et al. | |
| 2008/0314322 A1 | 12/2008 | Stellnert et al. | |
| 2009/0032090 A1* | 2/2009 | Kats | F24J 2/542 136/251 |
| 2010/0116895 A1 | 5/2010 | Kures | |
| 2010/0180884 A1 | 7/2010 | Oosting | |
| 2010/0185553 A1* | 7/2010 | Fischer | G06F 17/30734 705/348 |
| 2010/0206302 A1 | 8/2010 | Cheung et al. | |
| 2011/0021133 A1 | 1/2011 | Zwern | |
| 2011/0041784 A1 | 2/2011 | McAlister | |
| 2011/0048502 A1 | 3/2011 | Kikinis et al. | |
| 2011/0073161 A1 | 3/2011 | Scanlon | |
| 2011/0114079 A1 | 5/2011 | Heckendorn | |
| 2011/0308512 A1 | 12/2011 | Nakasato et al. | |
| 2012/0067338 A1 | 3/2012 | Funcheon | |
| 2012/0085340 A1 | 4/2012 | Hinderling | |
| 2012/0227729 A1 | 9/2012 | Lundahl et al. | |
| 2012/0325201 A1 | 12/2012 | Deng | |
| 2013/0098425 A1 | 4/2013 | Amin et al. | |
| 2013/0340846 A1 | 12/2013 | Peel et al. | |
| 2014/0196761 A1* | 7/2014 | Tilley | G05B 15/02 136/246 |
| 2014/0201109 A1* | 7/2014 | Tilley | G05B 15/02 705/412 |
| 2015/0159914 A1 | 6/2015 | Michael | |
| 2015/0357970 A1 | 12/2015 | Mao et al. | |
| 2016/0154082 A1* | 6/2016 | Plourde | G01S 3/7861 250/203.4 |
| 2017/0025989 A1* | 1/2017 | Shaw | H02S 20/32 |
| 2018/0054186 A1* | 2/2018 | Chen | H03H 17/04 |

FOREIGN PATENT DOCUMENTS

| | | |
|---|---|---|
| EP | 2293378 | 3/2011 |
| GB | 2469321 | 10/2010 |
| WO | 9313396 | 7/1993 |
| WO | 2008092195 | 8/2008 |
| WO | 2011035037 | 3/2011 |
| WO | 2016089885 | 6/2016 |

OTHER PUBLICATIONS

International Search Report and Written Opinion for related PCT Application No. PCT/US2015/063208 dated May 6, 2016 (16 pages).
Invitation to Pay Additional Fees for related PCT/US2018/022826 dated Jun. 27, 2018 (13 pages).
International Search Report and Written Opinion for related PCT Application No. PCT/US2017/062558 dated Mar. 29, 2018 (19 pages).
International Search Report and Written Opinion for related PCT Application No. PCT/US2018/022826 dated Aug. 20, 2018 (20 pages).
Invitation to Pay Additional Fees for related PCT/US2017/062558 dated Feb. 5, 2018 (14 pages).

* cited by examiner

DUAL AXIS TRACKING DEVICE

CROSS-REFERENCE TO RELATED APPLICATIONS

The present application claims priority to U.S. Provisional Patent Application No. 62/085,699 filed on Dec. 1, 2014, entitled Mathematical Model for the Inactivation of Biological Contaminates Using Solar Heating and U.S. Provisional Patent Application No. 62/259,748 filed on Nov. 25, 2015, entitled Fluid Heating System, the content of each of which are hereby incorporated by reference herein in their entireties.

FIELD OF THE INVENTION

The present application is generally directed to systems and methods for tracking a moving object in space. Particularly, the present application is directed to tracking an object as it moves across the sky and directing a payload toward the object. More particularly, the present application is directed to systems and methods for continuously or intermittently determining the location of an object as it moves across the sky, and repositioning the payload to direct it toward the moving object.

BACKGROUND OF THE INVENTION

The background description provided herein is for the purpose of generally presenting the context of the disclosure. Work of the presently named inventors, to the extent it is described in this background section, as well as aspects of the description that may not otherwise qualify as prior art at the time of filing, are neither expressly nor impliedly admitted as prior art against the present disclosure.

In various applications, it may be desirable to track a star, planet, or other object as it moves across the sky during the course of a day. For example, solar light or radiation may be collected by directing one or more solar panels at the sun. While some solar panels are maintained as stationary objects, others may be configured to track the sun as it moves across the sky, so as to increase the quantity of sunlight or solar radiation collected. Traditional solar tracking mechanisms may operate with one or more axes of movement. Multiple axes of movement may, in some cases, be more efficient than a single axis of movement by allowing for more precise positioning. In some cases, solar panels may be moved on circular or rotational tracks in order to follow the sun's movement across the sky throughout a day. For example, some solar tracking mechanisms may operate with an altazimuth, or altitude/azimuth, motion system. An altazimuth motion system may provide for rotation about a vertical axis, such as a load bearing mast, and separate rotation about a horizontal axis.

Various methods and systems may be used to calculate a location of an object in the sky, such as the sun, at which to direct a device on the earth, such as a solar panel. Often, such systems and methods may be individually designed to operate at a particular location on the earth's surface. In some cases, for example, a system for tracking the sun's movement that is developed for use in the earth's Northern Hemisphere may not function as accurately in the Southern Hemisphere. In some embodiments, tracking mechanisms such as solar tracking mechanisms may track based on polar coordinates, or may use both latitudinal and longitudinal axes, for example. Moreover, some conventional tracking systems may use high cost motors such as digital servo motors to generate motion.

BRIEF SUMMARY OF THE INVENTION

The following presents a simplified summary of one or more embodiments of the present disclosure in order to provide a basic understanding of such embodiments. This summary is not an extensive overview of all contemplated embodiments, and is intended to neither identify key or critical elements of all embodiments, nor delineate the scope of any or all embodiments.

The present disclosure, in one or more embodiments, relates to a tracking device for tracking the location of a moving object. The tracking device may include a spine portion for carrying a payload, a first linear actuation assembly causing the payload to rotate about a first axis of rotation, a second linear actuation assembly causing the payload to rotate about a second axis of rotation, and a control module configured to determine a position of a moving object in the sky and operate the first and second linear actuation assemblies to direct the payload relative to the moving object. In some embodiments, the first and second linear actuation assemblies may each include a linear actuator and a motor. In some embodiments, each linear actuation assembly may further include a linear absolute encoder. The second axis of rotation may align with a longitudinal axis of the spine portion in some embodiments. Further, the first axis of rotation may be orthogonal to the second axis of rotation. In some embodiments, the tracking device may also have an upright portion supporting the spine portion, an arm portion between the spine portion and upright portion, and a single axis support coupling the spine portion to the upright portion. The first actuation assembly may be coupled to the upright portion and pivotably coupled to the arm portion. Likewise, the second actuation assembly may be coupled to the arm portion and pivotably coupled to the spine portion with a torque arm. The spine portion may remain static with respect to a third axis of rotation defined as a vertical axis aligned with the upright portion. In some embodiments, the tracking device may be configured for wireless communication.

Additionally, the present disclosure, in one or more embodiment, relates to a solar tracking device for tracking the location of the sun over a period of time. The solar tracking device may have a spine portion carrying at least one of a solar panel, a solar concentrator, and a heliostat. The tracking device may further have a first linear actuation assembly causing the one or more solar panels to rotate about a first axis of rotation, a second linear actuation assembly causing the one or more solar panels to rotate about a second axis of rotation, and a control module. The control module may be configured to receive Global Positioning System data comprising the tracking device's location, the time, and the date. The control module may further be configured to determine the location of the sun based on the Global Positioning System data, and direct the first and second actuation assemblies to position the one or more solar panels such that the one or more solar panels are directed relative to the sun. In some embodiments, the first and second linear actuation assemblies may each have a linear actuator and a motor. In some embodiments, the first and second linear actuation assemblies may each have a linear absolute encoder. In some embodiments, the second axis of rotation may align with a longitudinal axis of the spine portion, and the first axis of rotation may be orthogonal to the second axis of rotation. The tracking device may further have an upright portion supporting the spine portion, an arm portion between the spine portion and the upright portion, and a single axis support coupling the arm portion to the upright portion. The first actuation assembly may be coupled to the upright portion and pivotably coupled to the arm portion. Similarly, the second actuation assembly may be coupled to the arm portion and pivotably coupled to the torque arm. The spine portion may have a first end and a second end. In some embodiments, the first end may be directed North and the second end may be directed South. In some embodiments, the tracking device may be configured for wireless communication. In some embodiments, directing the first and second actuation assemblies may include referencing an error correction lookup table.

Additionally, in one or more embodiments, the present disclosure relates to a method for directing a payload relative to a moving object. The method may include the steps of receiving Global Positioning System data related to the time, date, and location of a tracking device, determining an azimuth and altitude of the moving object with respect to the tracking device, calculating a first angular motion path corresponding to a first axis of rotation of the payload and a second angular motion path corresponding to a second axis of rotation of the payload, calculating a first linear motion path and a second linear motion path from the first and second angular motion paths, and directing the device to rotate the payload in accordance with the first and second linear motion paths. In some embodiments, the method may be repeated at timed intervals over the course of a day. In some embodiments, the method may further include calculating an error correction for the first linear motion path and the second linear motion path. The error correction may be determined by referencing an error correction lookup table and using bicubic interpolation to interpolate the error correction.

Additionally, in one or more embodiments, the present disclosure relates to a tower structure having a tracking device for tracking the location of a moving object. The tracking device may include a spine portion for carrying a payload, a first linear actuation assembly causing the payload to rotate about a first axis of rotation, a second linear actuation assembly causing the payload to rotate about a second axis of rotation, and a control module configured to determine a position of a moving object in the sky. The control module may be further configured to operate the first and second linear actuation assemblies to direct the payload relative to the moving object. In some embodiments, the tower structure may be a communication tower or a solar power tower. Where the tower structure is a solar power tower, the payload may include a heliostat in some embodiments.

While multiple embodiments are disclosed, still other embodiments of the present disclosure will become apparent to those skilled in the art from the following detailed description, which shows and describes illustrative embodiments of the invention. As will be realized, the various embodiments of the present disclosure are capable of modifications in various obvious aspects, all without departing from the spirit and scope of the present disclosure. Accordingly, the drawings and detailed description are to be regarded as illustrative in nature and not restrictive.

BRIEF DESCRIPTION OF THE DRAWINGS

While the specification concludes with claims particularly pointing out and distinctly claiming the subject matter that is regarded as forming the various embodiments of the present disclosure, it is believed that the invention will be better understood from the following description taken in conjunction with the accompanying Figures, in which:

DETAILED DESCRIPTION

The present disclosure, in one or more embodiments, relates to a device for tracking movement of an object in space. More particularly, the present disclosure relates to a device for tracking an object's movement across the sky, based on Global Positioning System (GPS) information. The tracking device may function through the use of one or more, and in some cases two, linear actuation assemblies. The tracking device may generally be configured to accurately track the location of the sun, or another object in space, from any location on the earth, such that the tracking device may direct a payload, such as solar panels, solar concentrators, or heliostats toward the object or at an angle relative to the object. In some embodiments, the tracking device may call for a relatively low power consumption. In some embodiments, the tracking device may have a wireless device such as a Zigbee radio to allow for wireless communication.

Figure 1:
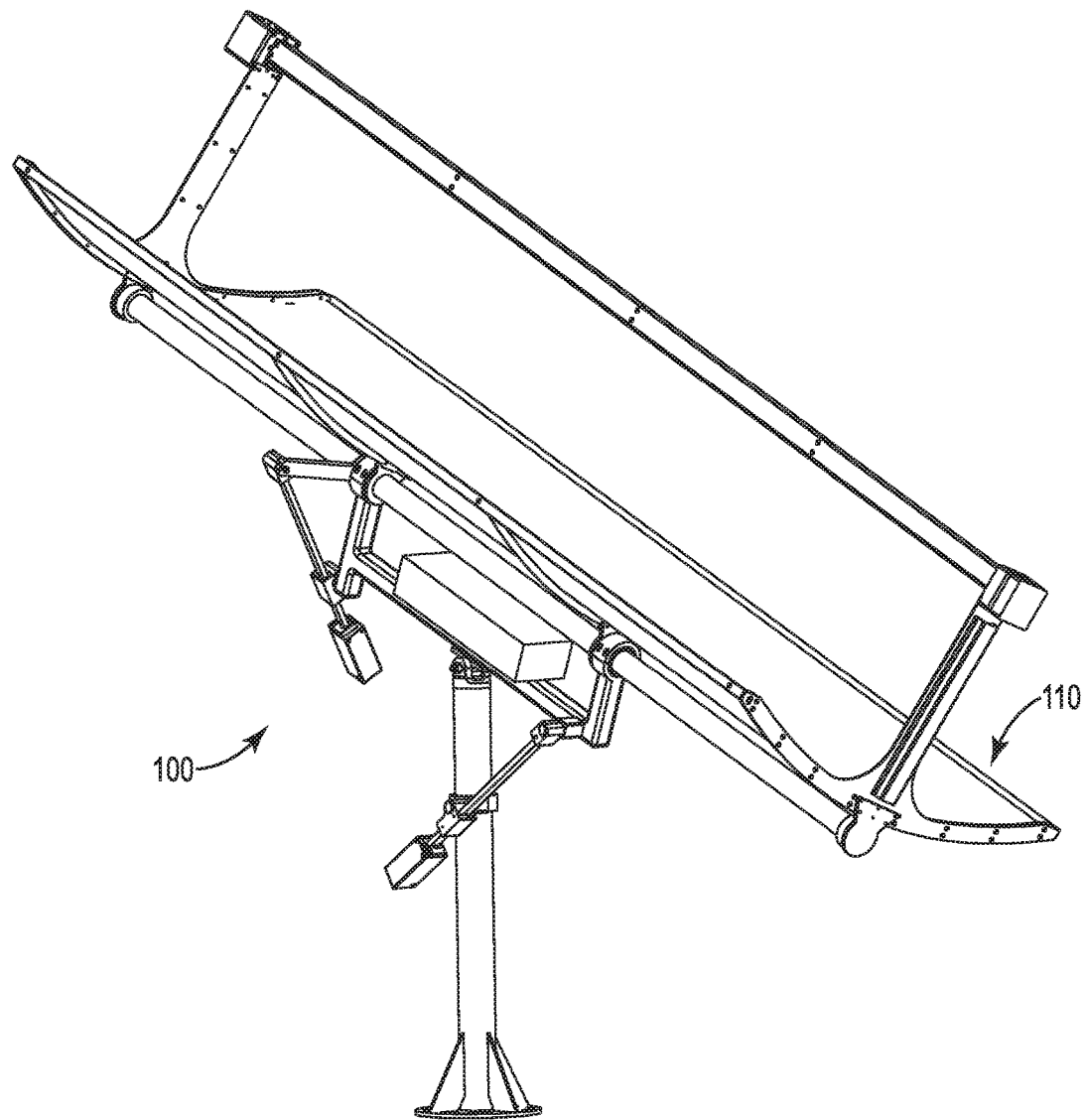
FIG. 1 is a perspective view of a tracking device and payload, according to some embodiments.

Turning now to FIG. 1, a dual axis tracking device 100 is shown. The tracking device 100 may generally be configured to track the location of an object in space, such as the sun, such that the device may direct a payload 110, such as solar panels, toward the object or at an angle relative to the object. The tracking device 100 may track the location of the object over the course of a day or night, for example, as the object moves across the sky, such that the device may substantially continuously direct its payload 110 at the appropriate angle.

Figure 2:
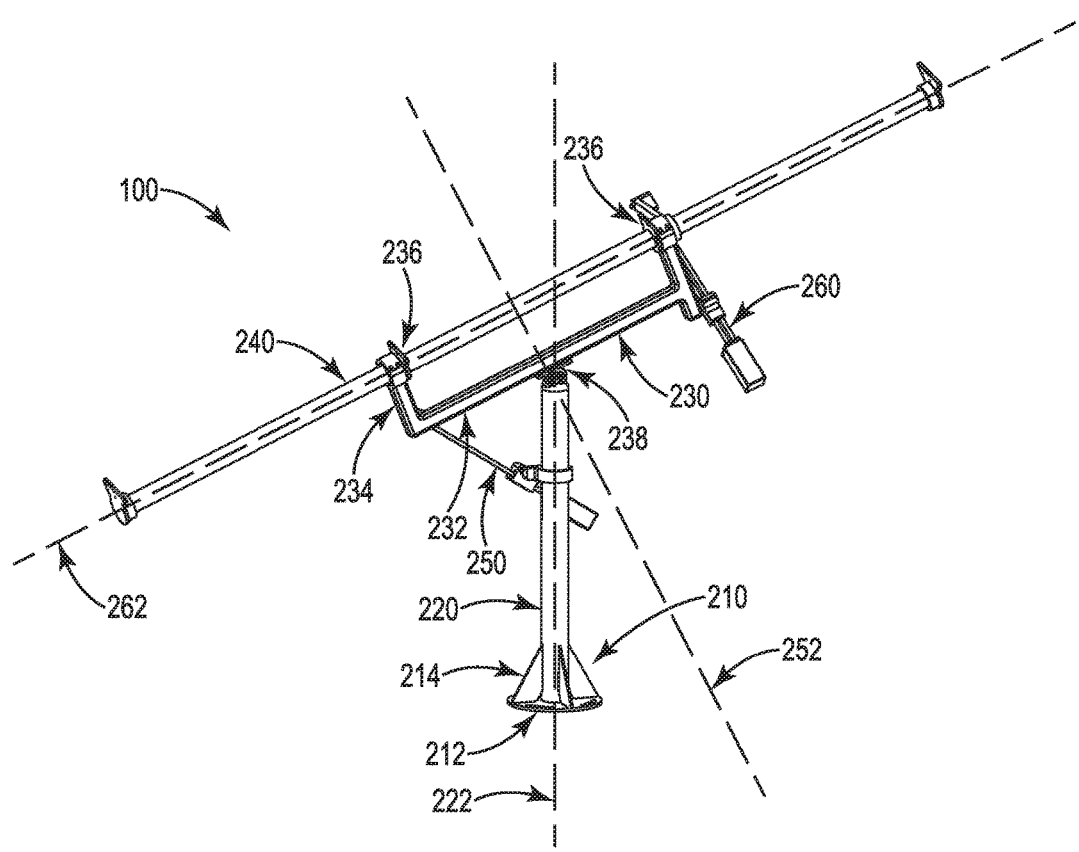
FIG. 2 is a perspective view of the tracking device of FIG. 1.

FIG. 2 illustrates the tracking device 100 that may support and direct the payload 110. The tracking device 100 may have a base 210, an upright portion 220, an arm portion 230, a spine portion 240, a first actuation assembly 250, and a second actuation assembly 260.

The upright portion 220 may generally support the weight of the tracking device 100 and any payload 110 the device may be carrying such as solar panels. The upright portion 220 may support the tracking device 100 high enough off of the ground surface so as to allow for a full range of movement of the payload 110 by the first 250 and second 260 actuation assemblies. In some embodiments, the upright portion 220 may generally be constructed of steel, aluminum, or other metals or metal alloys. In other embodiments, the upright portion 220 may be constructed of one or more plastics such as PVC, concrete, or any other suitable material. The upright portion 220 may generally have any suitable length. The upright portion 220 may have a rounded cross section as shown in FIG. 2, in some embodiments. In other embodiments, the upright portion 220 may have any suitable cross sectional shape. The upright portion 220 may have any suitable width or diameter. The upright portion 220 may connect with or to the ground surface via a base 210.

With continued reference to FIG. 2, the base 210 may provide lateral support for the upright portion 220. The base 210 may include a foot 212 and one or more angular supports 214. In some embodiments, the tracking device 100 may be positioned on the ground surface. In other embodiments, the tracking device 100 may be positioned on a foundation, such as a concrete foundation, or other surface. The foot 212 may be positioned between the upright portion 220 and ground surface, foundation, or other surface. The foot 212 may have a width or diameter that is larger than that of the upright portion 220, so as to provide lateral support to the upright portion. In some embodiments, the foot 212 may be bolted or otherwise coupled to the ground, foundation, or other surface. In other embodiments, the foot 212 may be positioned on the ground, foundation, or other surface without a coupling mechanism. Where the foot 212 is not bolted or otherwise coupled to the ground, foundation, or other surface, the foot may have a relatively large width or diameter, compared to the upright portion 220. However, where the foot 212 is bolted or otherwise coupled to the ground, foundation, or other surface, the foot may have a relatively smaller width or diameter, in some embodiments. In other embodiments, the foot 212 may have any suitable width or diameter. As shown in FIG. 2, in some embodiments, the foot 212 may have a circular shape. In other embodiments, the foot 212 may have any suitable shape. The foot 212 may generally have any suitable thickness. One or more angular supports 214 may strengthen the connection between the foot 212 and the upright portion 220. The one or more angular supports 214 may have any suitable thickness. In some embodiments, the base 220 may be constructed of steel, aluminum, or other metals or metal alloys. In other embodiments, the base 220 may be constructed of one or more plastics such as PVC, concrete, or any other suitable material.

With continued reference to FIG. 2, an arm portion 230 may couple to the upright portion 220 to provide rotational support to the spine portion 240. The arm portion 230 may have a lateral member 232 and one or more connector arms 234. In some embodiments, the lateral member 232 may be positioned parallel to the spine portion 240. In some embodiments, the lateral member 232 may have a length that is longer, shorter, or the same as the length of the spine portion 240. Generally, the lateral member 232 may have a length sufficient to provide enough support for the length of the spine portion 240, and the length of the lateral member may thus be proportion to the length of the spine portion. The one or more connector arms 234 may extend perpendicular from the lateral member 232 to connect to the spine portion 240. In some embodiments, as shown in FIG. 2, the arm portion 230 may have one connector arm 234 at each end of the lateral member 232. In other embodiments, the arm portion 230 may have any suitable number of connector arms 234. Each connector arm 234 may couple to the spine portion 240 via a connector 236. The connector 236 may be or include a clamp, bolts, screws, or any suitable coupling mechanism. In some embodiments, the connector 236 may allow the spine portion 240 to rotate or twist. In some embodiments, the spine portion 240 may connect directly to the lateral member 232. For example, in some embodiments, the spine portion 240 may pass through an opening in the lateral member 232. The lateral member 232 and connector arms 234 may have any suitable cross sectional shape, such as a rectangular shape for example. The arm portion 230 may be constructed of steel, aluminum, or other metals or metal alloys. In other embodiments, the arm portion 230 may be constructed of one or more plastics such as PVC, or any other suitable material.

In some embodiments, the arm portion 230 may couple to the upright portion 220 by a single axis support 238. The single axis support 238 may comprise a pivoted connection and may provide for rotational movement about one or more axes, and in some cases two axes. In some embodiments, the single axis support 238 may allow for the arm portion 230 to rotate about a first axis of rotation 252, which may be perpendicular to a longitudinal axis of the lateral member 232, and a second axis of rotation 262 orthogonal to the first axis. The first and second axes of rotation 252, 262 may each pass through the connection point between the arm portion 230 and the upright portion 220. In some embodiments, the spine portion 240 may connect directly to the upright portion 230 via the single axis support 238.

With continued reference to FIG. 2, the spine portion 240 may provide support and/or alignment for a payload 110 held by the tracking device 100. For example, the device may carry one or more solar panels, in which the spine portion 240 may provide a base for supporting and/or aligning the one or more solar panels. In this way, as the object is tracked across the sky, the spine portion 240 may serve to align the payload 110 with the object or with a point relative to the object. The spine portion 240 may be any suitable length and width or diameter so as to provide sufficient support to the payload 110. The spine portion 240 may have any suitable cross sectional shape, such as a circular shape for example. The spine portion 240 may be constructed of steel, aluminum, or other metals or metal alloys. In other embodiments, the spine portion 240 may be constructed of one or more plastics such as PVC, or any other suitable material.

With continued reference to FIG. 2, the tracking device 100 may have one or more actuation assemblies that facilitate movement of the device. Generally, one or more actuation assemblies may facilitate movement of the arm portion 230, spine portion 240, and/or payload 110 with respect to the upright portion 220 and base 210. In some embodiments, the tracking device 100 may have a first actuation assembly 250 and a second actuation assembly 260.

The first actuation assembly 250 may, in some embodiments, be positioned between the upright portion 220 and the arm portion 230. In other embodiments, the first actuation assembly 250 may be positioned between the spine portion 240 and the upright portion 220, or between the arm portion 230 and spine portion 240, for example. Other positioning arrangements of the first actuation assembly 250 are contemplated as well. The first actuation assembly 250 may facilitate movement of the arm portion 230, spine portion 240, and/or payload 110 with respect to the upright portion 220 and base 210 about a horizontal axis. The first actuation assembly 250 may couple to the upright portion 220 and arm portion 230 using clamps, bolts, screws, or any suitable coupling mechanism. In some embodiments, the first actuation assembly 250 may couple to the upright portion 220 and/or arm portion 230 with a pivoted, hinged, or other movable connection.

In some embodiments, the second actuation assembly 260 may be positioned between the arm portion 230 and the spine portion 240. In other embodiments, the second actuation assembly 260 may be positioned between the arm portion 230 and the upright portion 220, or between the spine portion 240 and the upright portion 220, for example. Other positioning arrangements of the second actuation assembly 260 is contemplated as well. The second actuation assembly 260 may facilitate movement of the arm portion 230, spine portion 240, and/or payload 110 with respect to the upright portion 220 and base 210 about the longitudinal axis of the spine. The second actuation assembly 260 may couple to the upright arm portion 230 and spine portion 240 using clamps, bolts, screws, or any suitable coupling mechanism. In some embodiments, the second actuation assembly 260 may couple to the arm portion 230 and/or spine portion 240 with a pivoted, hinged, or other movable connection.

Using the first and second actuation assemblies 250, 260, the tracking device 100 may operate to position the spine portion 240 to direct a payload 110 toward or relative to a moving object, such as the sun. In this regard, the first actuation assembly 250 may provide for movement of the arm portion 230, spine portion 240, and/or payload 110 about a first axis of rotation 252, as shown in FIG. 2. The first axis of rotation 252 may be perpendicular to a longitudinal axis of the spine portion 240 and may be generally horizontal. Additionally, in some embodiments, the second actuation assembly 260 may provide for movement of the payload 110 about a second axis of rotation 262, which may be the longitudinal axis of the spine. The two axes of rotation 252, 262 may allow for the tracking device 100 to direct its payload 110 at a moving object across the sky, in some embodiments, while the longitudinal axis of the spine portion 240 remains statically pointed in a direction. That is, where a third axis 222 aligns with the upright portion 220, the longitudinal axis of the spine portion 240 may remain fixed with respect to rotation about the third axis. For example, where the longitudinal axis of the spine portion 240 is directed North and South, the third axis 222 and rotation about the third axis may be static such that the longitudinal axis of the spine portion may continuously point North and South while movement about the first and second axes 252, 262 occurs.

Figure 3A:
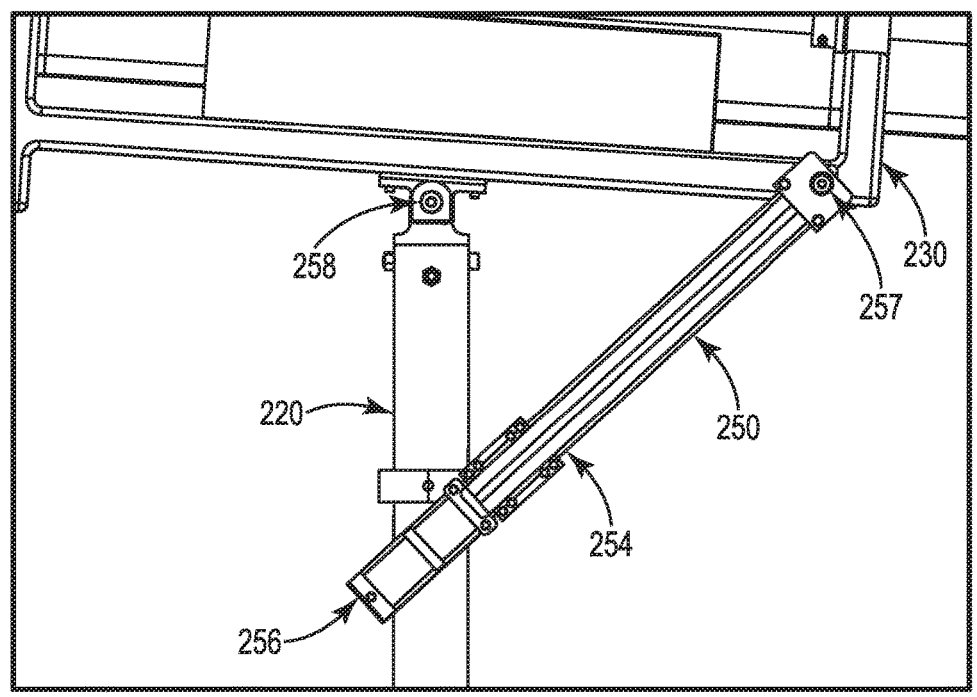
FIG. 3A is a detail view of a first actuation assembly, according to some embodiments.

FIG. 3A illustrates the first actuation assembly 250. The first actuation assembly 250 may rotate the arm portion 230, spine portion 240, and/or payload 110 about the first axis of rotation 252 with two pivot points 257, 258. The first pivot point 257 may be located where the first actuation assembly 250 couples to the atm portion 230. The second pivot point 258 may be located where the arm portion 230 connects to the upright portion 220 via the single axis support 238. The first actuation assembly may comprise a linear actuator 254, such as a linear slide, and a motor 256 that drives the linear actuator. A sliding element of the linear actuator 254 may couple to the upright portion 220 with a fixed connection. In this way, as the motor 256 drives movement along the linear actuator 254, the arm portion 230, spine portion 240, and/or payload 110 may pivot about the first and second pivot points 257, 258, and be rotated about the first axis of rotation 252. It may be appreciated that the orientation of the linear actuator 254 may be reversed in some embodiments, such that the sliding element may couple to the arm portion 230 and a pivot point may be located at the connection between the first actuation assembly 250 and the upright portion 220. The linear actuator 254 may have any suitable length and range of motion in various embodiments. In some embodiments, the length may depend on where along the arm portion 230 and upright portion 220 the first actuation assembly 250 connects, and may further depend on the range of motion provided about the first axis of rotation 252.

The motor 256 may be a relatively inexpensive motor in some embodiments. For example, the motor 256 may be a low cost stepper motor. In other embodiments, a DC motor or servo motor may be used. In other embodiments, the motor 256 may be any suitable motor. The motor 256 may rotate a gear screw or lead screw, for example, with each step. The gear screw or lead screw may operate to drive the sliding element along the linear actuator 254. In this way, the gear screw or lead screw may translate the rotational motion of the motor 256 into linear motion of the linear actuator 254. In some embodiments, the gear screw or lead screw may couple to a gearbox, which may operate to drive the sliding element along the linear actuator 254. The gearbox may provide for additional torque to the linear actuator 254 in some embodiments. A gearbox may include one or more gears arranged in any suitable configuration. In some embodiments, a planetary gearbox may be used. In other embodiments, any suitable gearbox may be used to assist with moving the sliding element along the linear actuator 254. In some embodiments, any suitable gear reduction of the gearbox may be used to increase the motor and gearbox output torque.

In some embodiments, the motor 256, linear actuator 254, and/or other components may be configured for use in harsh conditions or otherwise outdoor use. For example, mechanical components may be configured to operate without lubricating agents. In some embodiments, for example, the gear screw or lead screw may connect to the linear actuator 254 with a plastic bearing or other element that may function without lubrication, such as for example an IGUS DRYLIN bearing or other device to assist with movement. In some embodiments, the gear screw or lead screw or one or more other components may be constructed of a material such as that used in the IGUS DRYLIN devices. In other embodiments, similar materials or any suitable material may be used to provide for operation without lubricating agents.

Figure 3B:
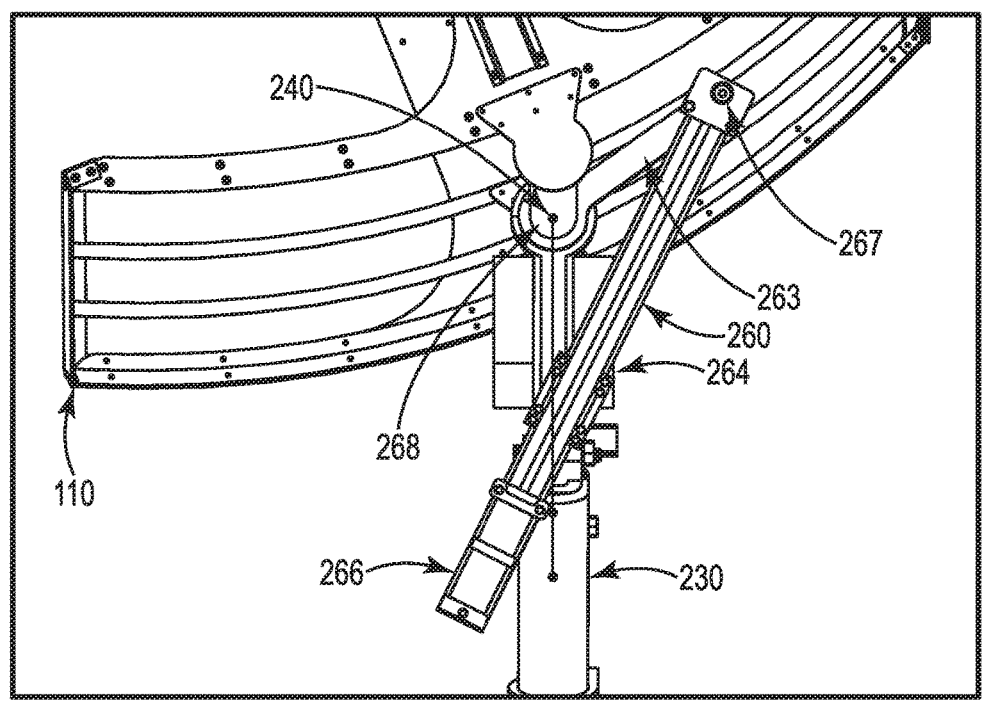
FIG. 3B is a detail view of a second actuation assembly, according to some embodiments.

FIG. 3B illustrates the second actuation assembly 260. The second actuation assembly 260 may twist the spine portion 240 so as to rotate the payload 110 about the second axis of rotation 262. Like the first actuation assembly 250, the second actuation assembly 260 may comprise a linear actuator 264 and a motor 266 that drives the linear actuator. The second actuation assembly 260 may further comprise a torque arm 263 in some embodiments. The torque arm may connect the linear actuator to the spine portion 240. The second actuation assembly may connect to the upright portion 220 with a fixed connection, in some embodiments. In this way, the second actuation assembly 260 may rotate the spine portion 240 and/or payload 110 about the second axis of rotation 262 with two pivot points 267, 268. The first pivot point 267 may be located where the second actuation assembly 260 couples to the torque arm 263. The second pivot point 268 may be located where the torque arm 263 couples to the spine portion 240. A sliding element of the linear actuator 264 may couple to the upright portion 220 with a fixed connection. In this way, as the motor 266 drives movement along the linear actuator 264, the spine portion 240 and/or payload 110 may pivot about the first and second pivot points 267, 268, and be rotated about the second axis of rotation 262. It may be appreciated that the orientation of the linear actuator 264 may be reversed in some embodiments, such that the sliding element may couple to the spine portion 240 and a pivot point may be located at the connection between the second actuation assembly 260 and the upright portion 220. The linear actuator 264 may have any suitable length and range of motion in various embodiments. In some embodiments, the length may depend on where along the spine portion 240 and upright portion 220 the second actuation assembly 260 connects, and may further depend on the range of motion provided about the second axis of rotation 262.

Like motor 256 of the first actuation assembly 250, the motor 266 of the second actuation assembly 260 may be a relatively inexpensive motor in some embodiments. For example, the motor 266 may be a low cost stepper motor. In other embodiments, a DC motor or servo motor may be used. In other embodiments, the motor 266 may be any suitable motor. The motor 266 may rotate a gear screw or lead screw, for example, with each step. The gear screw or lead screw may operate to drive the sliding element along the linear actuator 264. In this way, gear screw or lead screw may translate the rotational motion of the motor 266 into linear motion of the linear actuator 264. As with motor 256, in some embodiments, the gear screw or lead screw may couple to a gearbox, which may operate to drive the sliding element along the linear actuator 264. The gearbox may provide for additional torque to the linear actuator 264 in some embodiments. A gearbox may include one or more gears arranged in any suitable configuration. In some embodiments, a planetary gearbox may be used. In other embodiments, any suitable gearbox may be used to assist with moving the sliding element along the linear actuator 264. In some embodiments, any suitable gear reduction of the gearbox may be used to increase the motor and gearbox output torque.

In some embodiments, the motor 266, linear actuator 264, and/or other components may be configured for use in harsh conditions or otherwise outdoor use. For example, mechanical components may be configured to operate without lubricating agents. In some embodiments, for example, the gear screw or lead screw may connect to the linear actuator 264 with a plastic bearing or other element that may function without lubrication, such as for example an IGUS DRYLIN bearing or other device to assist with movement. In some embodiments, the gear screw or lead screw or one or more other components may be constructed of a material such as that used in the IGUS DRYLIN devices. In other embodiments, similar materials or any suitable material may be used to provide for operation without lubricating agents.

In some embodiments, the tracking device 100 may be connected to a power source. The power source may operate the motors 256, 266 of the first and second actuation assemblies 250, 260. The power source may consist of AC and/or DC power, such as battery power, or other power sources in some embodiments. The power source may additionally power a control module in some embodiments.

Figure 9:
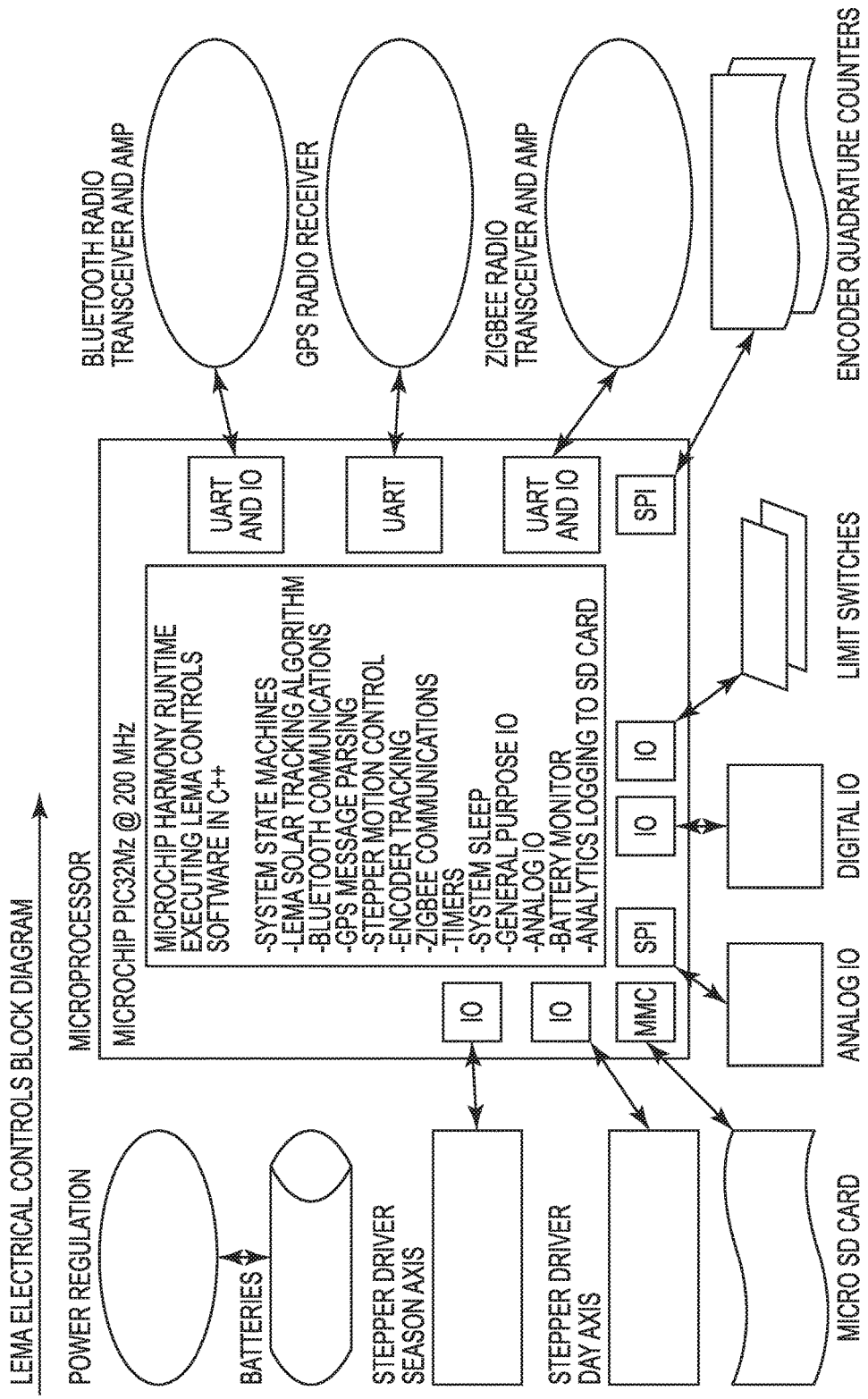
FIG. 9 is a block diagram of a control module, according to some embodiments.

In some embodiments, the tracking device 100 may be connected to a control module. The control module may consist of hardware and/or software components. The control module may be connected to the motors 256, 266 in some embodiments. In some embodiments, the control module may determine an approximate position of an object moving across the sky, such as the sun. The control module may include a GPS system in some embodiment, which may include hardware and/or software, such that the control module can determine where on the earth it is located and the local time of day and date. The control module may use hardware and/or software to determine the position of an object in space, such as the sun, from the GPS information. For example, the control module may be configured to determine the azimuth and altitude of the sun from the location of the tracking device 100, as discussed more fully below. The control module may additionally or alternatively be configured to send instructions to the motors 256, 266 to drive the first and second actuation assemblies 250, 260. For example, the control module may instruct the motors 256, 266 to position the payload 110 to be directed toward or relative to the moving object, such as the sun. In some embodiments, the control module may include any or all of the elements shown in FIG. 9. It should be understood that the particular elements shown in FIG. 9 are illustrated as examples. In other embodiments, the control module may include elements similar or related to those shown in FIG. 9 or other elements not depicted in FIG. 9.

Figure 4:
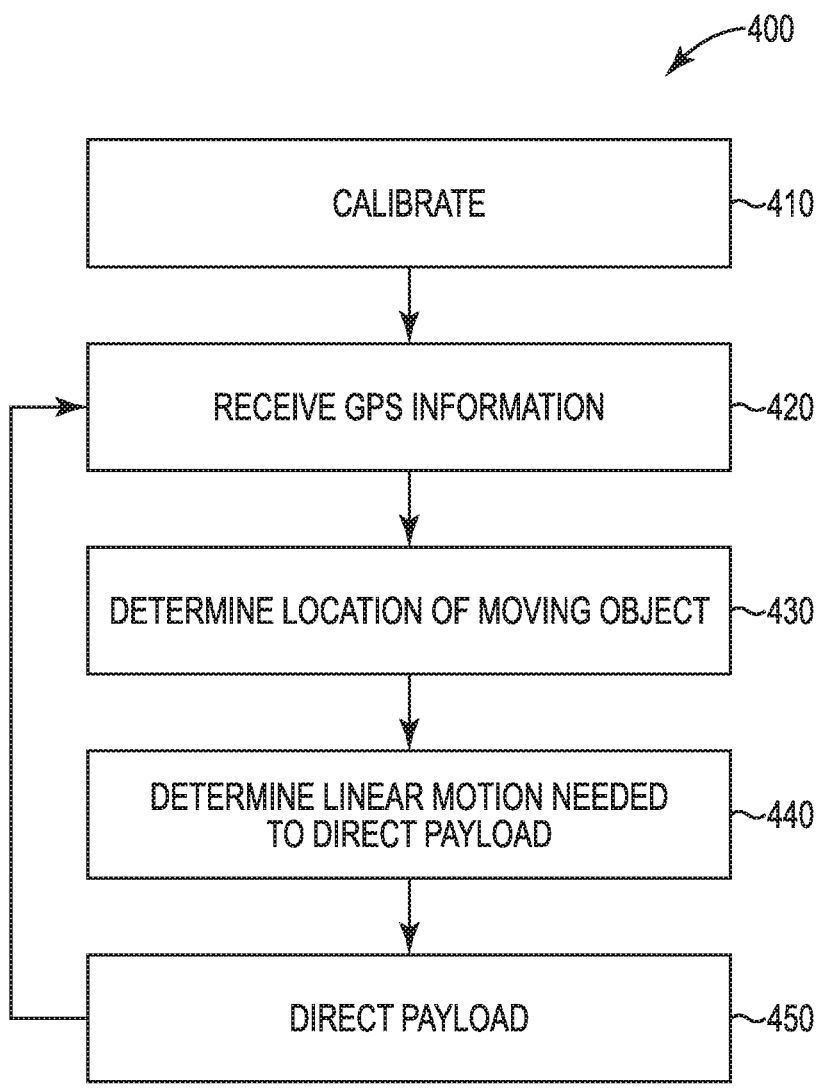
FIG. 4 is a flow diagram depicting a method of tracking a moving object and directing a payload toward the object, according to some embodiments.

In use, the tracking device may operate to track the location of an object and direct the payload toward or relative to that object. For example, in some embodiments, the tracking device may use GPS information to determine the location of the device, and from that information, the location of the sun. For example, the tracking device may use such GPS information as a triangulated location, time, and date to determine an altitude and azimuth of an object in space, such as the sun. The tracking device may additionally or alternatively operate to direct its payload, such as one or more solar panels, toward the determined location of the object in space by way of the first and second actuation assemblies. In other embodiments, the tracking device may operate to direct its payload toward a location or object relative to the determined location of the object ins pace by way of the first and second actuation assemblies. Various algorithms may be used to determine an altitude and azimuth based on GPS information. Once the azimuth and altitude are known, the location can be converted into a first motion path, performed by the first actuation assembly, and a second motion path, performed by the second actuation assembly. FIG. 4 illustrates a method 400 that the tracking device may perform in some embodiments. The method may include a calibration step (410), receiving GPS information (420), determining location of the object in space, such as the sun (430), determining positioning of the device (440), and positioning the device (450).

In some embodiments, the device may perform a calibration step (410). In some embodiments, the calibration step may be performed automatically. For example, the calibration step may be performed automatically when the tracking device initially powers on at a location. In other embodiments, the calibration may be performed based on some user input. In some embodiments, the calibration step may be performed partially or entirely manually. The calibration step may include determining one or more assumptions. That is, in some embodiments, the tracking device may operate, at least in part, based on one or more assumptions. For example, in some embodiments, an assumption may be that the longitudinal axis of the spine portion 240 is directed North at one end and directed South at an opposing end. Such assumptions may provide for more accurate positioning of the spine portion and/or payload in some embodiments. Based on these assumptions, the tracking device may be used to track the location of an object from any location on the earth's surface. A correct assumption (such as a first end of the longitudinal axis of the spinal portion is directed North in the Northern Hemisphere) may allow the tracking device to accurately track the location of a moving object and direct its payload accordingly. In this way, it may be appreciated that the tracking device may be able to track the location of an object from any location on the earth's surface merely by changing the assumption(s). For example, an assumption in the Northern Hemisphere may be that a first end of the spinal portion is directed North. For operation in the Southern Hemisphere, the assumption may be changed to reflect that the first end of the spinal portion is directed South.

The calibration step (410) may additionally or alternatively include homing the first and second actuation assemblies. Homing an actuation assembly may include operating the motor, such as a stepper motor, to one end of travel until the motor reaches a limit switch, such as an electromechanical limit switch, defining a limit of travel for the linear actuator. The tracking device may register the point of the limit switch as a zero point of motion of the actuation assembly. Positioning of the device may then be determined based on the zero points of motion for each actuation assembly. This may allow the control module to more accurately determine the relationship between the motor operation and the positioning of the spine portion and/or payload. In some embodiments, once the calibration step is completed, the tracking device may be able to power off and on without the need for recalibration. In some embodiments, the tracking device may know its position each time it turns on after calibration because the actuation assemblies may have a zero back drive. That is, in some embodiments, each actuation assembly may have sufficient forces preventing the linear actuator and/or drive screw or lead screw from moving without the motor drive enabled. In some embodiments, where for example the motors are stepper motors, the motors may additionally or alternatively help to prevent the linear actuators and/or drive screws or lead screws from moving during shut off. Further, in some embodiments, the gearbox may additionally or alternatively help to prevent the linear actuators and/or drive screws or lead screws from moving during shut off.

In some embodiments, a device such as a rotary encoder or linear absolute encoder may be used to determine a position of the linear actuator with respect to the motor operation. In some embodiments, a linear absolute encoder or other similar device may provide a location of the linear actuator to the tracking device, such that the tracking device may know the position of the linear actuator with respect to the motor. In this way, the linear absolute encoder may, at least in part, reduce or obviate the need for homing an actuation assembly. For example, the linear absolute encoder may provide a position of a linear actuator when the tracking device powers on, when the device begins a tracking routine, at the request of the tracking device or a user, and/or at any other suitable time. Each actuation assembly may operate using a linear absolute encoder in some embodiments. The use of one or more linear absolute encoders or similar device may allow the tracking device to correct for any intentional or unintentional movement of the actuation assemblies that may occur during power shut offs or between tracking routines, for example.

As shown in FIG. 4, the tracking device may receive GPS information (420). In some embodiments, the GPS information may be received at the tracking device from a source. For example, the GPS information may be sent to the tracking device over a wired or wireless network. In other embodiments, the device may have GPS hardware and/or software, as discussed above, and may determine the GPS information internally using, for example, data transmitted by a GPS satellite constellation and received by onboard GPS antenna and hardware. GPS information may include location information such as triangulated coordinates, date, and time, each related to the tracking device's current location. Using the GPS information, the tracking device may determine its exact or approximate location on the surface of the earth.

Figure 5A:
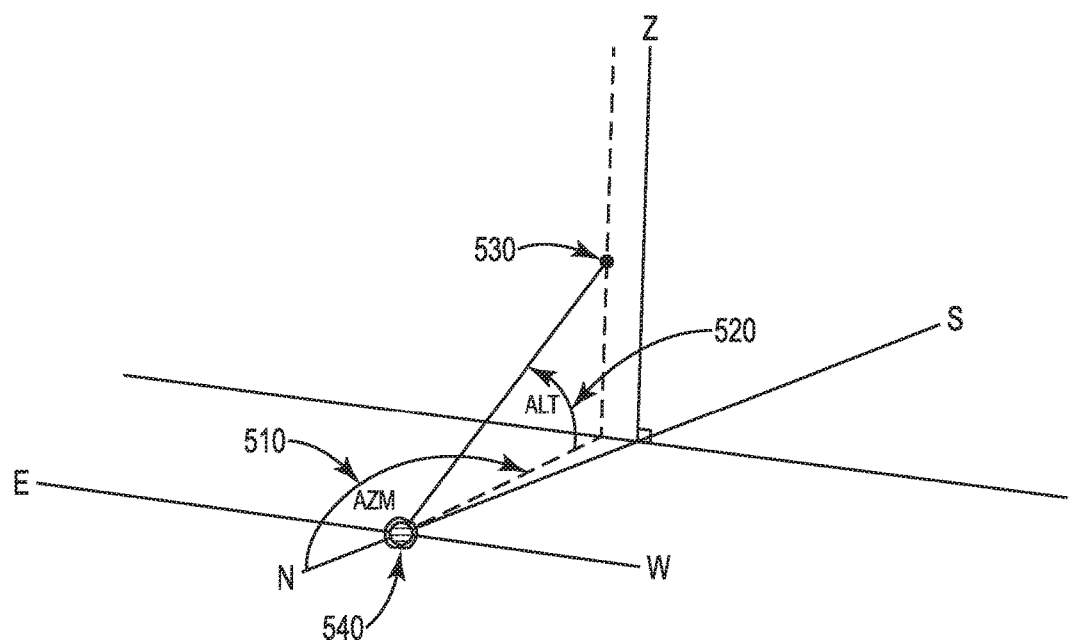
FIG. 5A is a graphical representation of an azimuth and altitude of an object in relation to a tracking device, as viewed from the Northern Hemisphere, according to some embodiments.
Figure 5B:
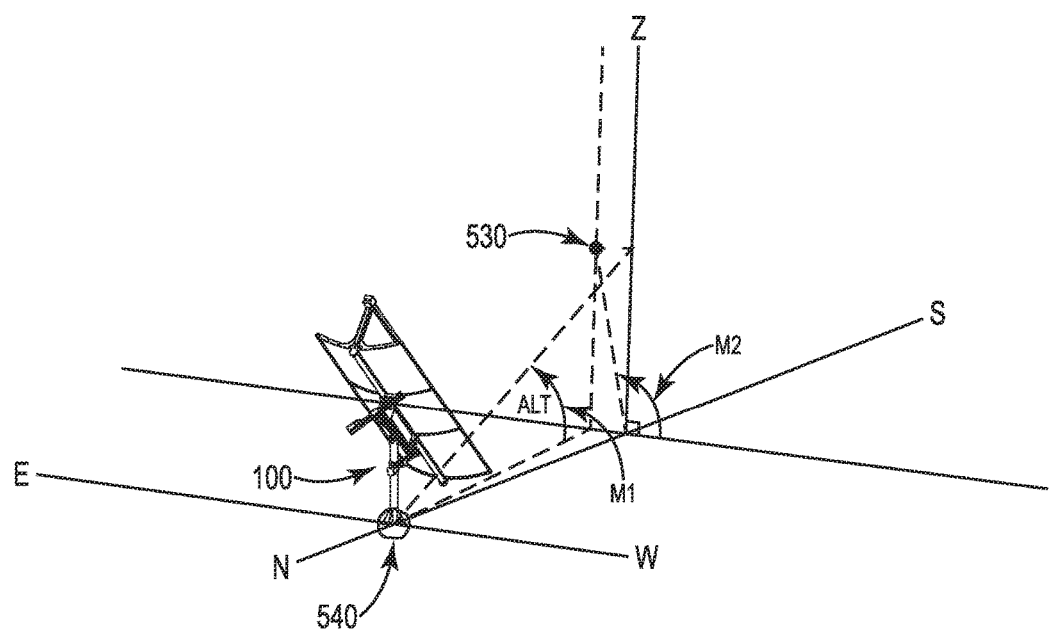
FIG. 5B is a graphical representation of a first and second motion paths of a tracking device, based on the azimuth and altitude of FIG. 6, according to some embodiments.
Figure 6:
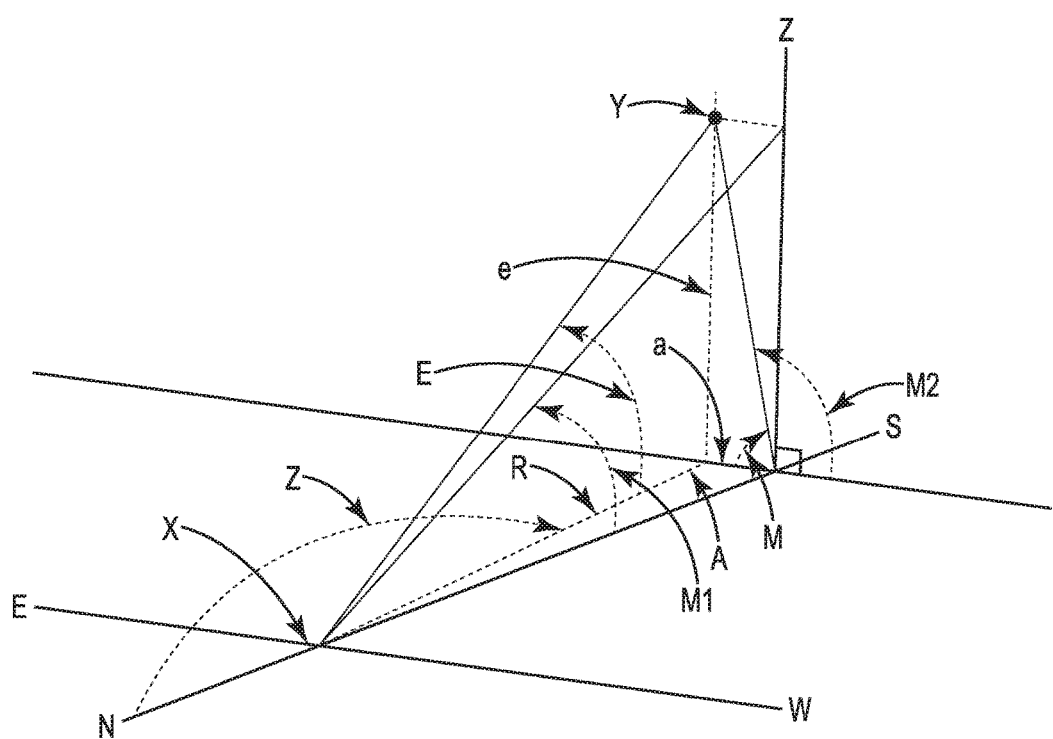
FIG. 6 is a graphical representation of the calculation of the first motion path and the second motion path, according to some embodiments.

Based on the received GPS information, the tracking device may determine the location of a moving object in space, such as the sun (430). For example, the tracking device may determine an azimuth and altitude of an object in relation to the device's position. Where the moving object is the sun, the azimuth and altitude may be calculated from the GPS information based on a Solar Position Algorithm, provided by the U.S. Department of Energy, for example. In other embodiments, other calculations or methods may be used to determine the azimuth and altitude of an object or other location information. FIG. 5A graphically illustrates the location of an azimuth 510 and altitude 520 in relation to a location 530 of an object in space, such as the sun, and the location 540 of the tracking device 100. Both locations 530, 540 are shown in relation to North, South, East, and West directions and in relation to a vertical Z axis. The azimuth 510 and altitude 520 combine to provide the location vector 530 of the sun or other object. FIG. 5B graphically illustrates the angle of the first motion path M1, related to the first actuation assembly 250, and the angle of the second motion path M2, related to the second actuation assembly 260. FIG. 6 graphically illustrates the variables used to calculate the angles of the first motion path M1 and the second motion path M2, according to some embodiments. In some embodiments, the angles of the motion paths M1, M2 may be calculated by the following:

$A = 180 - \text{Azimuth}$ $a = |\tan(A)|$ $R = \sqrt{1^2 + a^2}$ $e = R \tan(\text{Altitude})$ $$M = \tan^{-1} \frac{e}{a}$$

$M1 = \tan^{-1}(e)$ $M2 = \langle \text{if } A > 180 | M | 180 - M \rangle$

In other embodiments, other equations, calculations, or other methods may be used to determine the angles of the motion paths M1, M2. For example, in some embodiments, the calculation of M2 (i.e., the day axis angle) may be adjusted to accommodate the reference angle established by M1 (i.e., the season axis angle). In some embodiments, this may be performed by transforming the M2 back to an offset cylindrical coordinate system based on M1. This transforming would allow for higher accuracy at higher latitudes. Accordingly, by using a trigonometric transform to transform M2 back to an offset cylindrical coordinate system based on M1 and then calculating the M2 angle, the effect on M2 results in higher accuracy across a range of latitudes and seasons.

Figure 7A:
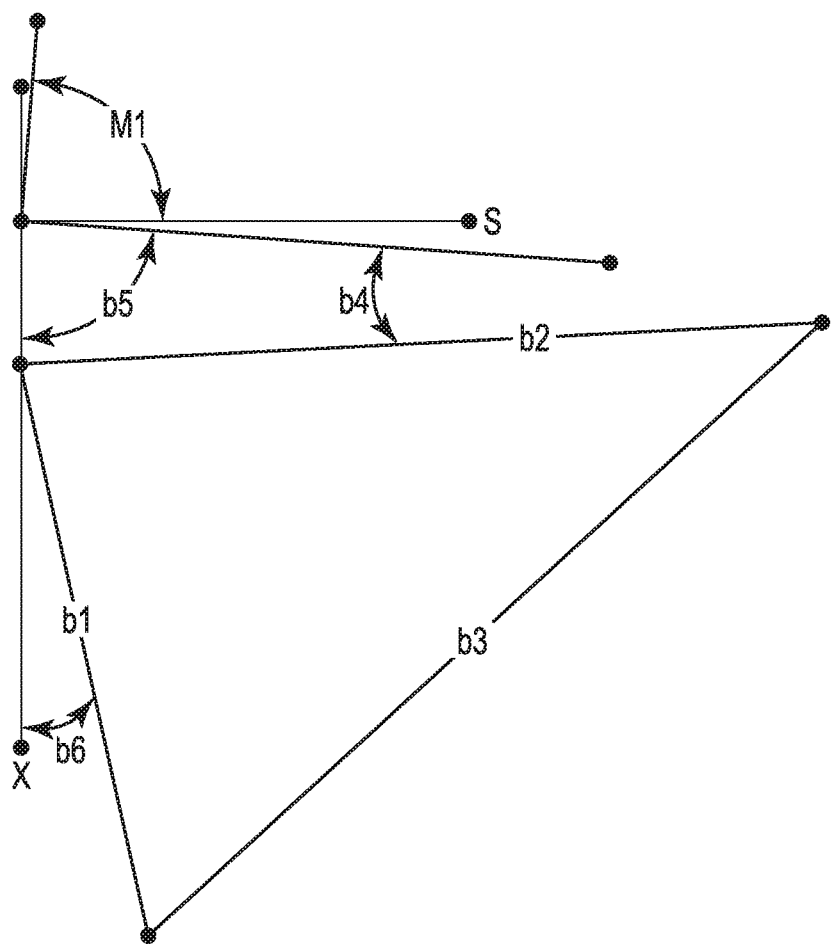
FIG. 7A is a graphical representation of the calculation of the first linear motion, according to some embodiments.
Figure 7B:
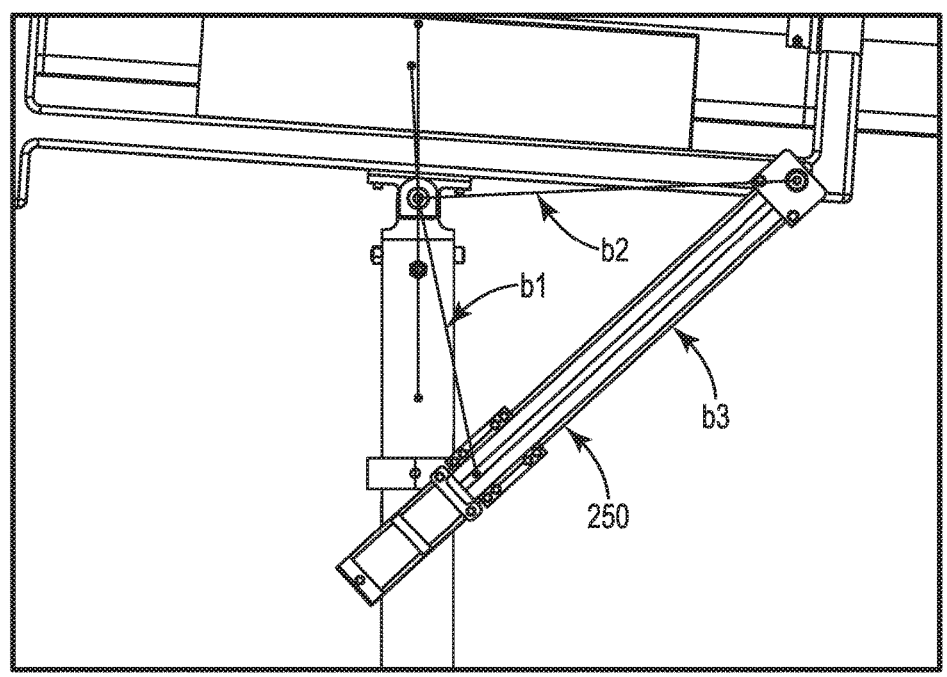
FIG. 7B is an illustration of the location of the variables used to calculate the first linear motion with respect to the first actuation assembly, according to some embodiments.

With continued reference to FIG. 4, from the angles of the motion paths M1, M2, the tracking device may determine where to direct the spine portion and/or payload, such that they are directed toward the object (440). For example, in some embodiments, the tracking device may determine a linear distance for each actuation assembly 250, 260 to direct the spine portion and/or payload toward the object. FIG. 7A graphically illustrates the variables used to calculate the first linear motion b3, according to some embodiments. In some embodiments, the first linear motion b3 may be calculated by the following:

$b2$=Length Torque Arm $b1$=Length Pivot Support $b4=M1-(b6-b4)$ $b3=\sqrt{(b1^2+b2^2-2*b1*b2)}$ $b3$=First Linear Motion FIG. 7B illustrates the locations of the torque arm length b2 and the pivot support length b1 in relation to the first actuation assembly 250. In other embodiments, the first linear motion b3 may be determined using other equations, calculations, or method.

Figure 8A:
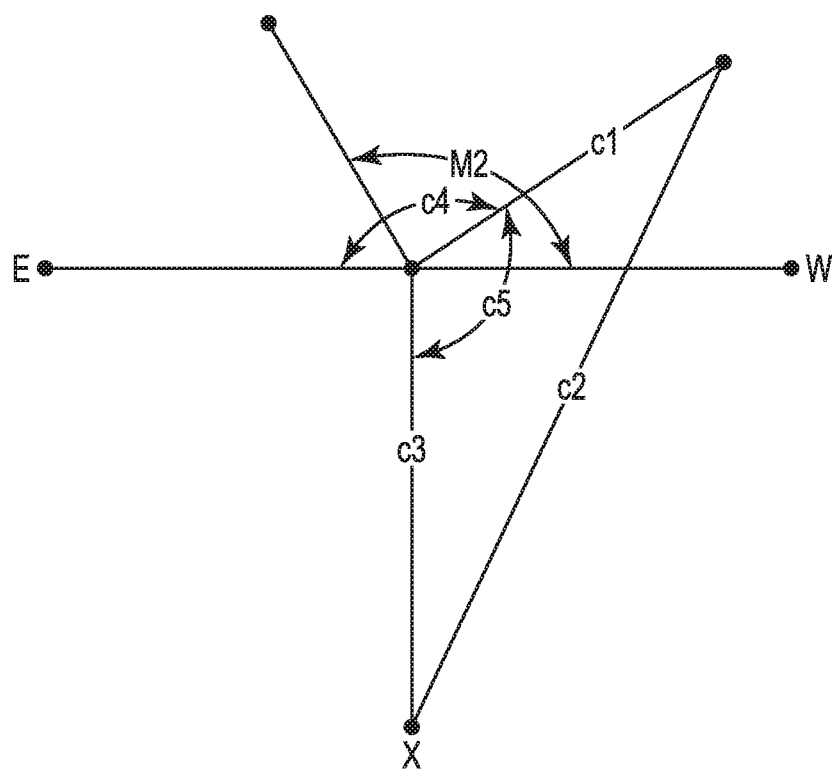
FIG. 8A is a graphical representation of the calculation of the second linear motion, according to some embodiments.
Figure 8B:
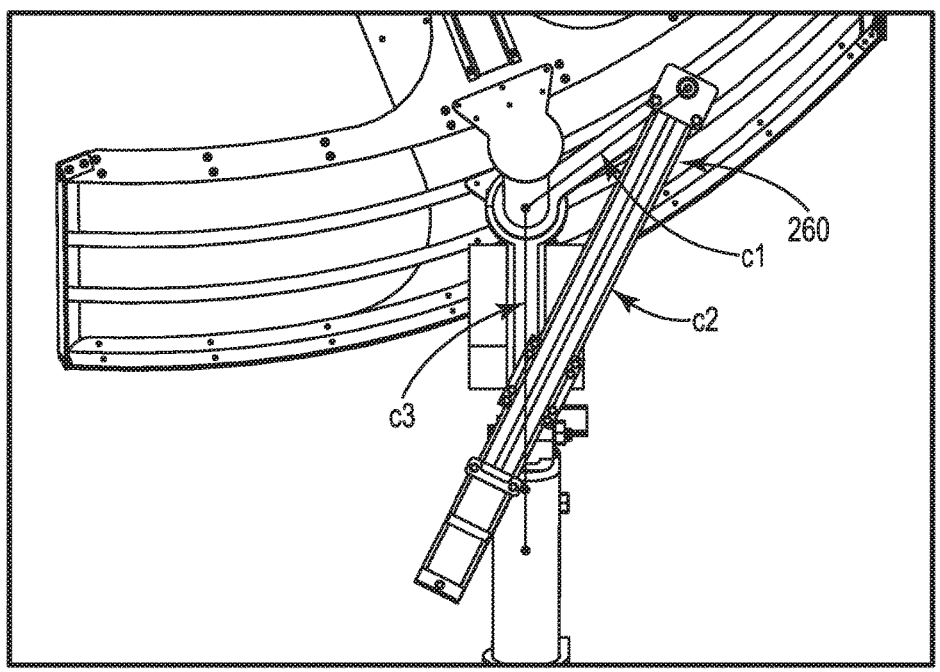
FIG. 8B is an illustration of the location of the variables used to calculate the second linear motion with respect to the second actuation assembly, according to some embodiments.

FIG. 8A. Graphically illustrates the variables used to calculate the second linear motion c2, according to some embodiments. In some embodiments, the second linear motion c2 may be calculated by the following:

$c1$=Length Torque Arm $c3$=Length Pivot Support $c5=M1+90$ $c2=\sqrt{(c1^2+c3^2-2*c1*c3)}$ $c2$=Second Linear Motion FIG. 8B illustrates the locations of the torque arm length c1 and the pivot support length c3 in relation to the second actuation assembly 260. In other embodiments, the second linear motion c2 may be determined using other equations, calculations, or methods. It may be appreciated that in other embodiments, the tracking device 100 may determine a direction for the payload by means other than linear motion. For example, the tracking device may angle the spine portion and/or payload from the ground surface, based on the first and second motion paths M1, M2.

It may be appreciated that the tracking device may be configured to direct its payload at an angle relative to the object moving across the sky. For example, in some embodiments, the payload may be a heliostat or similar device having a mirror or other reflective surface. The mirror or other reflective surface may be directed at an angle relative to the sun's location, such that it may reflect the sunlight toward another point which may be a stationary point. In such embodiments, the first and second linear motions may be calculated differently than above. That is, after determining the sun's azimuth and altitude, the tracking device may determine the first and second linear motions based on the location of the sun in the sky and an angle between the sun's location and the location of the point onto which the sunlight is to be reflected. Generally, the tracking device may be configured to direct its payload at any angle relative to the moving object's location. In this way, it may be appreciated that the tracking device may receive instructions to direct the payload toward generally any vector which may or may not depend on the location of the object being tracked. The instructions may be received locally or remotely over a wired or wireless network. It some embodiments, the positioning of the tracking device may be fully controlled remotely.

With the first and second linear motions b3, c2, the tracking device may instruct the motors to position the actuation assemblies so as to direct the payload toward the moving object or toward a different position (450). Where the motors are stepper motors, for example, the tracking device may determine a number of steps to operate on each motor, so as rotate the payload about the first and second axes of rotation 252, 262 to a desired position.

In some embodiments, the tracking device may repeat steps 420 through 450 intermittently or continuously. For example, in some embodiments, the tracking device may operate continuously to determine the location of the object in space and continuously update the device's positioning. In other embodiments, the tracking device may determine the object's location and reposition the device at intervals. For example, the tracking device may recalculate location and position every hour in some embodiments. In other embodiments, the tracking device may recalculate location and position every 15-45 minutes. In still other embodiments, the tracking device may recalculate location and position every 1-15 minutes in some embodiments. Particularly, the tracking device may recalculate location and position every 2-5 minutes in some embodiments. In this way, the device may take advantage of an object's relatively slow movement across the sky during the course of a day or night. For example, the location of the sun, may not move very far relative to the device over the course of a 2-5 minute interval. In other embodiments, the system may update location and position at different intervals. In this way, for example where the device is directing a payload of solar panels at the sun, the device may be able to recalculate intermittently without substantial solar collection efficiency loss. In addition, the ability to operate intermittently may allow the device to operate with relatively low power consumption. In some embodiments, a low power timer may operate to power the device on at intervals and then the device may power off after adjusting. The process of determining the sun's location and repositioning the device may be a relatively fast process, such that the device does not require much power when it powers on at intervals. For example, in some embodiments, over a twelve hour period of tracking the sun across the sky, the device may be powered off approximately 98% of the time.

In some embodiments, the tracking device may reference a calibration lookup table automatically or manually for purposes of error correction. A calibration lookup table may include a plurality of angles or motion paths relating to directing the payload and corresponding correction angles or correction paths, for example. That is, the lookup table may include error corrections to be performed by the first and/or second actuation assemblies for various calculated motion paths, angles, or object locations. The error corrections of the lookup table may allow the device to correct for various sources of error inherent in or otherwise found in the device. For example, error may be introduced by small inconsistencies in machining, motion of the linear actuator in response to each motor step, small calculation inaccuracies, which may relate to index of refraction of the atmosphere or other atmospheric conditions for example, and/or other sources of error. The lookup table may include a plurality of calculated positions or other calculations as performed by the tracking device, along with corresponding error corrections. In some embodiments, the lookup table may be determined based on actual device calculations performed over time, such as over the course of a day, month, or year, for example. The corresponding error corrections may be determined automatically or manually in some embodiments. Likewise, the lookup table may be populated automatically or manually. In some embodiments, the error corrections may be determined and/or populated in the lookup table using an application such as a mobile phone application. In some embodiments, error corrections may be determined for a limited number of location or position calculations, or for a period of time such as a day, for example, and additional error corrections may be extrapolated. In some embodiments, such calculations and extrapolations may be performed remotely using an application, such as a mobile phone or computer application. In some embodiments, an error correction lookup table or a portion thereof may be directly sent or supplied to the tracking device. In some embodiments, the tracking device may be automatically or manually directed to reference the lookup table periodically, such as after each location and position recalculation. In some embodiments, where a required error correction is not found on the lookup table for a particular calculated location, direction, or motion, bicubic interpolation or another interpolation method may be used to interpolate the needed error correction between two similar correction errors found in the lookup table.

Figure 10:
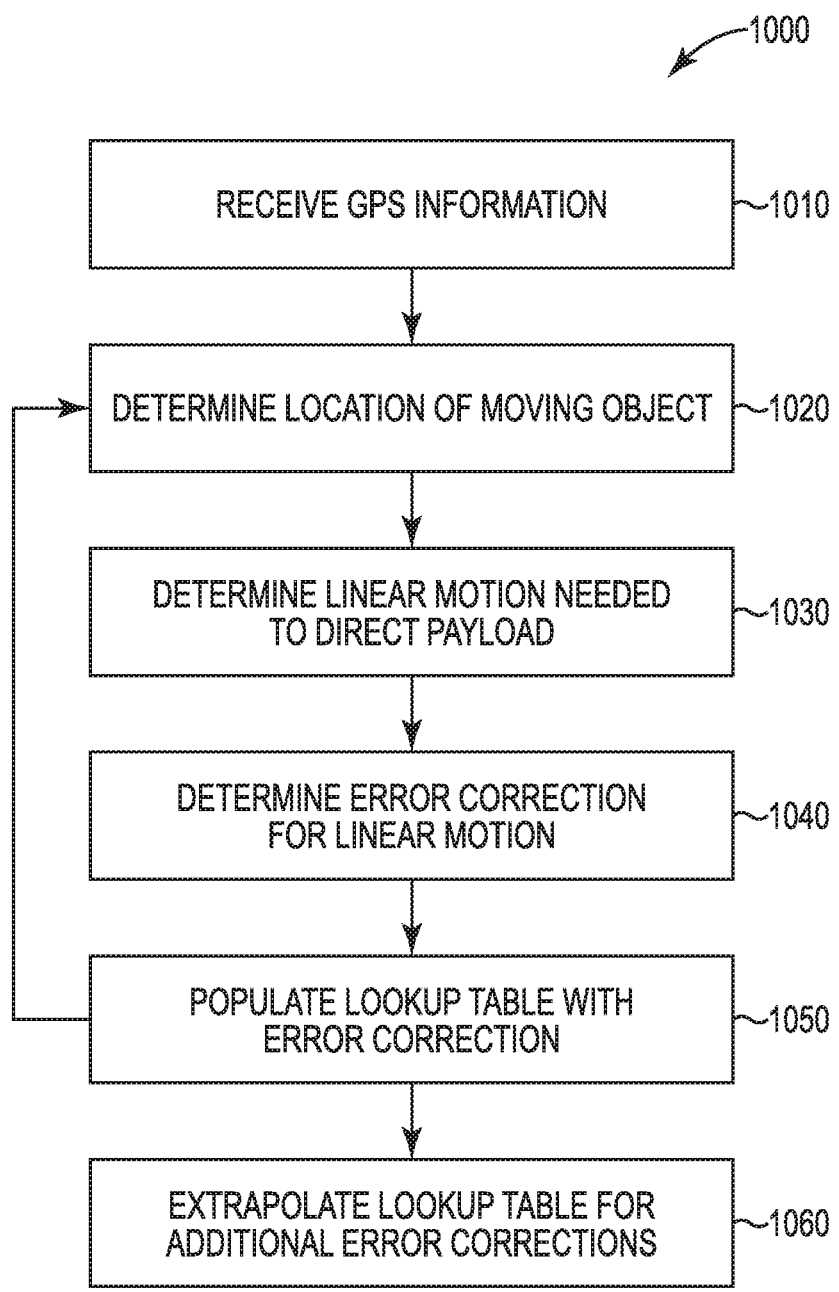
FIG. 10 is a flow diagram depicting a method of populating an error correction lookup table, according to some embodiments.

FIG. 10 illustrates a method 1000 for populating a lookup table with error corrections. As shown, the tracking device may receive GPS information (1010), determine a location of the moving object (1020), and determine a linear motion needed to direct the payload (1030), as described above with respect to method 400. Additionally, in some embodiments, an error correction for the linear motion may be determined (1040). The error correction may be determined automatically or manually, such as through the use of a mobile phone application or other application, locally or remotely. A lookup table may be populated with the determined error correction (1050). In some embodiments, steps 1020 through 1050 may be repeated until a plurality of data points are populated in the lookup table. In some embodiments, additional error corrections may be extrapolated to expand the lookup table (1060). Various extrapolation methods may be used in different embodiments.

Figure 11:
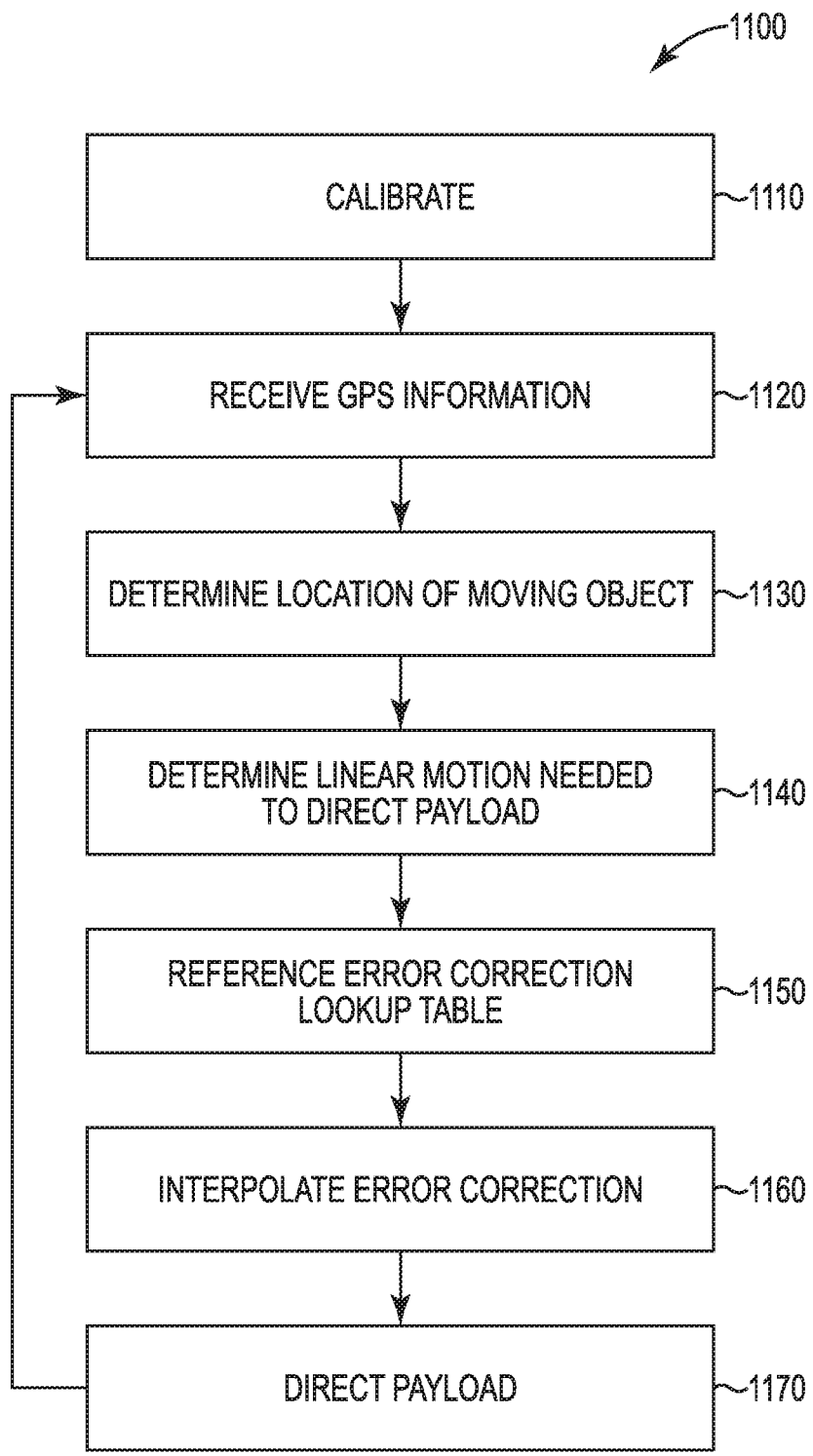
FIG. 11 is a flow diagram depicting a method of tracking a moving object and directing a payload toward the object, according to some embodiments.

FIG. 11 illustrates a method 1100 that the tracking device may perform in some embodiments in order to position the payload with consideration of the lookup table error corrections. As shown, the method 1100 may include a calibration step (1110), receiving GPS information (1120), determining a location of a moving object (1130), and determining a linear motion needed to direct the payload (1140), as described above with respect to method 400. Additionally, the method 1100 may include referencing an error correction lookup table (1150). The tracking device may be directed automatically or manually to reference the lookup table. Additionally, where needed in some embodiments, for example if the particular location or positioning does not fall within the error correction lookup table, the tracking device may interpolate an error correction (1160). Generally, any suitable interpolation method may be used, and in some embodiments, bicubic interpolation may be employed. Taking into account the error correction, the tracking device may direct its payload (1170) using one or more actuation assemblies. In some embodiments, steps 1120 through 1170 may be repeated intermittently or continuously, as described above in order to recalculate location of the tracked object and positioning of the tracking device.

It may be appreciated that the first and second actuation assemblies may relate generally to a season axis and a day axis in some embodiments. That is, the first actuation assembly, first axis of rotation, and first linear motion may be related to a seasonal position of the object being tracked. For example where the object being tracked is the sun, the sun's location may depend in part on the time of year. The positioning of the first actuation assembly may correlate with the sun's location during a particular time of year in some embodiments. Similarly, it may be appreciated that the second actuation assembly, second axis of rotation, and second linear motion may be related to a daily position of the object being tracked. For example where the object being tracked is the sun, the sun's location may depend in part on the time of day. The positioning of the second actuation assembly may correlate with the sun's location at a particular time of day in some embodiments. It may additionally be understood that while the first and second actuation assemblies may correlate generally with time of year and time of day, both actuation assemblies and axes of rotation may be used to direct the payload at any time of day or year. For example, although the first actuation assembly may generally correspond with seasonal location, the first actuation assembly may additionally rotate the payload about the first axis of rotation to track the object based on the time of day. That is, both actuation assemblies may be used to track the object's movement across the sky during the course of a day, for example.

In various embodiments, a tracking device of the present disclosure may be mounted to or generally located on a ground surface, a platform surface, or a tower surface or other structure, such as a cell phone or other communication tower or a solar power tower. For example, where the tracking device is mounted on a cell phone or other communication tower, the tracking device may track the location of a satellite and/or may direct its payload toward the satellite. In other embodiments, the tracking device may be located on a solar power tower, where the device may track the location of the sun and/or may direct its payload, such as mirror or other reflective surface, at an angle relative to the sun such that sunlight may be reflected toward a power collector or other device on the power tower. In such tower embodiments, the tracking device may be controlled or directed automatically and/or remotely, in some embodiments.

In some embodiments, the tracking device may operate, at least in part, over a wired or wireless network. A wireless connection may be, for example, an internet, Wi-Fi, Bluetooth, or other wireless connection. In some embodiments, the device may have a digital radio such as a Zigbee radio, which may allow the tracking device to communicate with one or more additional tracking devices or other communication devices over a wireless network. In this way, one or more tracking devices may be configured to share information, such as GPS information, tracking and positioning information, power consumption information, efficiency information, and/or other information over a wireless network. In some embodiments, the network and communication link may be maintained during power shut offs.

In some embodiments, the tracking device may receive an instruction to turn away from the object being tracked across the sky or otherwise away from its point of direction. For example, where the tracking device is tracking the sun to collect solar light or radiation, if the tracking device reaches some input or output limit or it is otherwise determined that solar light or radiation need not be collected for a period of time, the tracking device may be configured to receive an instruction to direct the payload away from the sun. Such an instruction may be received locally or remotely over a wired or wireless connection. For example, the instruction may be received from a device having a Zigbee radio. In some embodiments, the instruction may be received automatically when a sensor, for example, determines that the tracking device should stop collecting solar light or radiation. In other embodiments, the instruction may be input into the tracking device manually or may be received based on some user input.

In some embodiments, one tracking device may operate as a node to control one or more additional tracking devices. For example, one tracking device may aggregate the information received from multiple tracking devices. The single tracking device may direct and control positioning of the additional tracking devices, in some embodiments.

In some embodiments, a software application may allow a computing device to communicate with one or more tracking devices. A computing device may be a desktop or laptop computer, tablet, or mobile phone, for example. The software application may be used to communicate with one or more tracking devices over a wired or wireless network. The software application, such as a mobile device application for example, may allow a user to calibrate the tracking device locally or remotely. The application may further allow a user to collect data and/or provide user inputs locally or remotely.

In the foregoing description, a tracking device has been described. The tracking device may be configured to track an object in space, such as the sun, as the object moves across the sky. The tracking device may further be configured to direct a payload toward the object in space or toward an angle relative to the object in space. The tracking device may continuously or intermittently determine the location of the moving object, and adjust the position of the payload accordingly. The tracking device may calculate the position of the moving object based on GPS information, such as triangulated coordinates of the tracking device, date, and time. Generally, the tracking device may be capable of tracking an object such as the sun from anywhere on the earth's surface. The tracking device may employ one or more actuation assemblies to position the payload toward or relative to the moving object. The one or more actuation assemblies may operate through linear motion, in some embodiments. Moreover, the tracking device may operate with relatively low power consumption. The tracking device may communicate with one or more additional tracking devices or other communication devices over a wired or wireless network.

For purposes of this disclosure, any system described herein may include any instrumentality or aggregate of instrumentalities operable to compute, calculate, determine, classify, process, transmit, receive, retrieve, originate, switch, store, display, communicate, manifest, detect, record, reproduce, handle, or utilize any form of information, intelligence, or data for business, scientific, control, or other purposes. For example, a system or any portion thereof may be a personal computer (e.g., desktop or laptop), tablet computer, mobile device (e.g., personal digital assistant (PDA) or smart phone), server (e.g., blade server or rack server), a network storage device, or any other suitable device or combination of devices and may vary in size, shape, performance, functionality, and price. A system may include random access memory (RAM), one or more processing resources such as a central processing unit (CPU) or hardware or software control logic, ROM, and/or other types of nonvolatile memory. Additional components of a system may include one or more disk drives or one or more mass storage devices, one or more network ports for communicating with external devices as well as various input and output (I/O) devices, such as a keyboard, a mouse, touchscreen and/or a video display. Mass storage devices may include, but are not limited to, a hard disk drive, floppy disk drive, CD-ROM drive, smart drive, flash drive, or other types of non-volatile data storage, a plurality of storage devices, or any combination of storage devices. A system may include what is referred to as a user interface, which may generally include a display, mouse or other cursor control device, keyboard, button, touchpad, touch screen, microphone, camera, video recorder, speaker, LED, light, joystick, switch, buzzer, bell, and/or other user input/output device for communicating with one or more users or for entering information into the system. Output devices may include any type of device for presenting information to a user, including but not limited to, a computer monitor, flat-screen display, or other visual display, a printer, and/or speakers or any other device for providing information in audio form, such as a telephone, mobile phone, a plurality of output devices, or any combination of output devices. A system may also include one or more buses operable to transmit communications between the various hardware components. In some embodiments, a device or system of the present disclosure may include or operate using a field programmable gate array or other hardware having reconfigurable electrical circuitry such as one or more programmable logic blocks.

One or more programs or applications, such as a web browser, and/or other applications may be stored in one or more of the system data storage devices. Programs or applications may be loaded in part or in whole into a main memory or processor during execution by the processor. One or more processors may execute applications or programs to run systems or methods of the present disclosure, or portions thereof, stored as executable programs or program code in the memory, or received from the Internet or other network. Any commercial or freeware web browser or other application capable of retrieving content from a network and displaying pages or screens may be used. In some embodiments, a customized application may be used to access, display, and update information. In some embodiments, a software application may be used to update or upgrade operational code, programming, and/or firmware of systems or devices of the present disclosure. Such a software application may be a mobile phone application, a computer application, and/or may be accessible remotely via a wired or wireless data link.

Hardware and software components of the present disclosure, as discussed herein, may be integral portions of a single computer or server or may be connected parts of a computer network. The hardware and software components may be located within a single location or, in other embodiments, portions of the hardware and software components may be divided among a plurality of locations and connected directly or through a global computer information network, such as the Internet.

As will be appreciated by one of skill in the art, the various embodiments of the present disclosure may be embodied as a method (including, for example, a computer-implemented process, a business process, and/or any other process), apparatus (including, for example, a system, machine, device, computer program product, and/or the like), or a combination of the foregoing. Accordingly, embodiments of the present disclosure may take the form of an entirely hardware embodiment, an entirely software embodiment (including firmware, middleware, microcode, hardware description languages, etc.), or an embodiment combining software and hardware aspects. Furthermore, embodiments of the present disclosure may take the form of a computer program product on a computer-readable medium or computer-readable storage medium, having computer-executable program code embodied in the medium, that define processes or methods described herein. A processor or processors may perform the necessary tasks defined by the computer-executable program code. Computer-executable program code for carrying out operations of embodiments of the present disclosure may be written in an object oriented, scripted or unscripted programming language such as Java, Perl, PHP, Visual Basic, Smalltalk, C++, C#, VHDL, Verilog, or the like. However, the computer program code for carrying out operations of embodiments of the present disclosure may also be written in conventional procedural programming languages, such as the C, programming language, assembly language, or similar programming languages. A code segment may represent a procedure, a function, a subprogram, a program, a routine, a subroutine, a module, an object, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

In the context of this document, a computer readable medium may be any medium that can contain, store, communicate, or transport the program for use by or in connection with the systems disclosed herein. The computer-executable program code may be transmitted using any appropriate medium, including but not limited to the Internet, optical fiber cable, radio frequency (RF) signals or other wireless signals, or other mediums. The computer readable medium may be, for example but is not limited to, an electronic, magnetic, optical, electromagnetic, infrared, or semiconductor system, apparatus, or device. More specific examples of suitable computer readable medium include, but are not limited to, an electrical connection having one or more wires or a tangible storage medium such as a portable computer diskette, a hard disk, a random access memory (RAM), a read-only memory (ROM), an erasable programmable read-only memory (EPROM or Flash memory), a compact disc read-only memory (CD-ROM), or other optical or magnetic storage device. Computer-readable media includes, but is not to be confused with, computer-readable storage medium, which is intended to cover all physical, non-transitory, or similar embodiments of computer-readable media.

Various embodiments of the present disclosure may be described herein with reference to flowchart illustrations and/or block diagrams of methods, apparatus (systems), and computer program products. It is understood that each block of the flowchart illustrations and/or block diagrams, and/or combinations of blocks in the flowchart illustrations and/or block diagrams, can be implemented by computer-executable program code portions. These computer-executable program code portions may be provided to a processor of a general purpose computer, special purpose computer, or other programmable data processing apparatus to produce a particular machine, such that the code portions, which execute via the processor of the computer or other programmable data processing apparatus, create mechanisms for implementing the functions/acts specified in the flowchart and/or block diagram block or blocks. Alternatively, computer program implemented steps or acts may be combined with operator or human implemented steps or acts in order to carry out an embodiment of the invention.

Additionally, although a flowchart may illustrate a method as a sequential process, many of the operations in the flowcharts illustrated herein can be performed in parallel or concurrently. In addition, the order of the method steps illustrated in a flowchart may be rearranged for some embodiments. Similarly, a method illustrated in a flow chart could have additional steps not included therein or fewer steps than those shown. A method step may correspond to a method, a function, a procedure, a subroutine, a subprogram, etc.

As used herein, the terms "substantially" or "generally" refer to the complete or nearly complete extent or degree of an action, characteristic, property, state, structure, item, or result. For example, an object that is "substantially" or "generally" enclosed would mean that the object is either completely enclosed or nearly completely enclosed. The exact allowable degree of deviation from absolute completeness may in some cases depend on the specific context. However, generally speaking, the nearness of completion will be so as to have generally the same overall result as if absolute and total completion were obtained. The use of "substantially" or "generally" is equally applicable when used in a negative connotation to refer to the complete or near complete lack of an action, characteristic, property, state, structure, item, or result. For example, an element, combination, embodiment, or composition that is "substantially free of" or "generally free of" an ingredient or element may still actually contain such item as long as there is generally no measurable effect thereof.

In the foregoing description various embodiments of the present disclosure have been presented for the purpose of illustration and description. They are not intended to be exhaustive or to limit the invention to the precise form disclosed. Obvious modifications or variations are possible in light of the above teachings. The various embodiments were chosen and described to provide the best illustration of the principals of the disclosure and their practical application, and to enable one of ordinary skill in the art to utilize the various embodiments with various modifications as are suited to the particular use contemplated. All such modifications and variations are within the scope of the present disclosure as determined by the appended claims when interpreted in accordance with the breadth they are fairly, legally, and equitably entitled.

We claim:

1. A tracking device for tracking the location of a moving object, comprising:
    a spine portion supported by an upright support, for carrying a payload, and supported at a pivot connection, the spine portion defining a first axis of rotation extending along the spine and a second axis of rotation extending through the pivot connection perpendicular to the first axis of rotation;

a first linear actuation assembly causing the payload to rotate about the first axis of rotation;

a second linear actuation assembly causing the payload to rotate about the second axis of rotation; and a control module configured to determine a position of a moving object in the sky based on a position of the tracking device on the surface of a planet, the control module further configured to operate the first and second linear actuation assemblies to direct the payload relative to the moving object, by calculating an azimuth and altitude of the moving object and calculating a corresponding rotation about the first axis and the second axis, wherein calculating the rotation about the first axis is performed to accommodate the motion about the second axis.

2. The tracking device of claim 1, wherein the first linear actuation assembly and second linear actuation assembly each comprise a linear actuator and a motor.

3. The tracking device of claim 2, wherein the first linear actuation assembly and second linear actuation assembly each further comprise a linear absolute encoder.

4. The tracking device of claim 1, further comprising:
an arm portion between the spine portion and the upright portion; and
a single axis support coupling the arm portion to the upright portion.

5. The tracking device of claim 4, wherein the first actuation assembly is coupled to the upright portion and pivotably coupled to the arm portion.

6. The tracking device of claim 5, wherein the second actuation assembly is coupled to the arm portion and pivotably coupled to the spine portion with a torque arm.

7. The tracking device of claim 1, wherein the spine portion remains rotationally static with respect to a third axis defined as a vertical axis aligned with the upright portion.

8. The tracking device of claim 1, wherein the device is configured for wireless communication.

9. A solar tracking device for tracking the location of the sun over a period of time, comprising:
a spine portion supported by an upright support and carrying at least one of a solar panel, solar concentrator, and heliostat, the spine portion supported at a pivot connection, the spine portion defining a first axis of rotation extending along the spine and a second axis of rotation extending through the pivot connection perpendicular to the first axis of rotation;
a first linear actuation assembly causing the one or more solar panels to rotate about the first axis of rotation;
a second linear actuation assembly causing the one or more solar panels to rotate about the second axis of rotation; and
a control module configured to:
receive Global Positioning System data comprising the tracking device's location, the time, and the date;
determine the location of the sun based on the Global Positioning System data;
direct the first and second actuation assemblies to position the one or more solar panels such that the one or more solar panels are directed relative to the sun, by calculating an azimuth and altitude of the sun and calculating a corresponding rotation about the first axis and the second axis, wherein calculating the rotation about the first axis is performed to accommodate the rotation about the second axis.

10. The tracking device of claim 9, wherein the first linear actuation assembly and second linear actuation assembly each comprise a linear actuator and a motor.

11. The tracking device of claim 10, wherein the first linear actuation assembly and second linear actuation assembly each further comprise a linear absolute encoder.

12. The tracking device of claim 9, further comprising:
an arm portion between the spine portion and the upright portion; and
a single axis support coupling the arm portion to the upright portion.

13. The tracking device of claim 12, wherein the first actuation assembly is coupled to the upright portion and pivotably coupled to the arm portion.

14. The tracking device of claim 13, wherein the second actuation assembly is coupled to the arm portion and pivotably coupled to the spine portion with a torque arm.

15. The tracking device of claim 9, wherein the device is configured for wireless communication.

16. The tracking device of claim 9, wherein directing the first and second actuation assemblies comprises referencing an error correction lookup table.

17. A tower structure comprising a tracking device for tracking the location of a moving object, the tracking device comprising:
a spine portion supported by an upright support, for carrying a payload, and supported at a pivot connection, the spine portion defining a first axis of rotation extending along the spine and a second axis of rotation extending through the pivot connection perpendicular to the first axis of rotation;
a first linear actuation assembly causing the payload to rotate about the first axis of rotation;
a second linear actuation assembly causing the payload to rotate about the second axis of rotation; and
a control module configured to determine a position of a moving object in the sky based on a position of the tower structure on a surface of a planet, the control module further configured to operate the first and second linear actuation assemblies to direct the payload relative to the moving object, by calculating an azimuth and altitude of the moving object and calculating a corresponding rotation about the first axis and the second axis, where calculating the rotation about the first axis is performed to accommodate the rotation about the second axis.

18. The tower structure of claim 17, wherein the tower structure comprises a communication tower.

19. The tower structure of claim 17, wherein the tower structure comprises a solar power tower.

20. The tower structure of claim 19, wherein the payload comprises a heliostat.

* * * * *